United States Patent

Riechers et al.

[11] Patent Number: 6,153,797
[45] Date of Patent: Nov. 28, 2000

[54] RACEMIZING OF OPTICALLY ACTIVE AMINES

[75] Inventors: Hartmut Riechers, Neustadt; Joachim Simon, Mannheim; Arthur Höhn, Kirchheim; Andreas Kramer, Freinsheim; Frank Funke; Wolfgang Siegel, both of Limburgerhof; Christoph Nübling, Hassloch, all of Germany

[73] Assignee: BASF Aktiengesellschaft, Ludwigshafen, Germany

[21] Appl. No.: 09/259,043

[22] Filed: Mar. 1, 1999

[30] Foreign Application Priority Data

Feb. 12, 1998 [DE] Germany ............ 199 05 837

[51] Int. Cl.⁷ ............................ C07C 204/00
[52] U.S. Cl. ............................ 564/302
[58] Field of Search ................. 564/302

[56] References Cited

U.S. PATENT DOCUMENTS

| | | | |
|---|---|---|---|
| 3,954,870 | 5/1976 | Fukumaru et al. | 260/570 |
| 4,096,186 | 6/1978 | Ichikawa et al. | 260/584 |
| 4,990,666 | 2/1991 | Harsy | 564/302 |
| 5,847,215 | 12/1998 | Ditrich | 564/302 |

FOREIGN PATENT DOCUMENTS

| | | |
|---|---|---|
| 778260 | 6/1997 | European Pat. Off. . |
| 2851039 | 6/1980 | Germany . |
| 2903589 | 8/1980 | Germany . |
| 198 59 775 | 12/1998 | Germany . |
| 199 05 837 | 2/1999 | Germany . |
| 162213 | 4/1988 | India . |
| 6135906 | 5/1994 | Japan . |
| 98/03465 | 1/1998 | WIPO . |

OTHER PUBLICATIONS

Database WPI, Section Ch, Week 5821, Derwent AN 98–234725 (JP 10072410; Mar. 17, 1998).
Pat. Abst. of Japan, vol. 12, No. 467 (JP 63185943, Aug. 1, 1988).
Pat. Abst. of Japan, vol. 95, No. 10 (JP 07188120, Jul. 25, 1995).
Database WPI, Section Ch, Week 7908, Derwent Publications Ltd., London, GB: Class B05, AN 79–14874B, XP002112502 (English abstract of JP 54 005957, Jan. 17, 1979).
Database WPI, Section Ch, Week 9424, Derwent Publications Ltd., London, GB: Class B05, AN 94–197043, XP002112503 (English abstract of JP 06 135906, May 17, 1994).
U.S. aplication No., 09/303,599, Riechers et al., filed May 3, 1999.

*Primary Examiner*—Samuel Barts
*Attorney, Agent, or Firm*—Keil & Weinkauf

[57] ABSTRACT

In a process for racemizing optically active amines by reacting the optically active amine in the presence of hydrogen and a hydrogenation or dehydrogenation catalyst at elevated temperature, the reaction is carried out in liquid phase and the catalyst comprises the catalytically active constituents copper, silver, iron, cobalt, nickel, ruthenium, rhodium, palladium, osmium, iridium and/or platinum and a support material selected from the group consisting of aluminum oxide, zirconium dioxide, titanium dioxide, carbon and/or oxygen compounds of silicon.

9 Claims, No Drawings

RACEMIZING OF OPTICALLY ACTIVE AMINES

The present invention relates to a process for racemizing optically active amines of the formula I

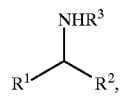
(I)

where $R^1$ and $R^2$ are different and $R^1$, $R^2$ and $R^3$ are alkyl, cycloalkyl, arylalkyl, aryl, heteroaryl or heterocyclic radicals and $R^3$, in addition, is hydrogen (H), where the radicals can bear substituents which are selected from the group consisting of alkyl, cycloalkyl, alkoxy, aryloxy, amino, alkylamino and dialkylamino, by reacting the optically active amine in the presence of hydrogen and a hydrogenation or dehydrogenation catalyst at elevated temperature.

Optically active amines of the formula I are, for example, valuable drugs and intermediates for preparing active compounds (cf., for example: DE-A-29 03 589, page 2, lines 17 to 26). Since, frequently, only one of the two enantiomers (based on the asymmetric carbon shown in I) is active, or is more active than the other enantiomer, processes for racemizing the less active enantiomer which arises, for example, in a racemate resolution of the corresponding racemic amine by known methods are required, because the more active enantiomer can be produced again from the racemized amine by known methods (e.g. racemate resolution).

IN-A-162 213 (Chem. Abstracts 110: 192247v) discloses a process for preparing racemic 2-aminobutanol by treating 1-2-aminobutanol with ammonia in the presence of $Rh/Al_2O_3$.

U.S. Pat. No. 4,096,186 describes a process for racemizing optically active aminoalcohols, in which the aminoalcohol is brought into contact with ammonia and hydrogen in the presence of a hydrogenation catalyst, which preferably comprises cobalt. In the reaction of optically active 2-amino-1-butanol, at a racemate yield of a maximum of 97.6%, a degree of racemization of only 63% is achieved. At a degree of racemization of 99%, in contrast, a racemate yield of only 75.1% is achieved.

U.S. Pat. No. 4,990,666 discloses a process for racemizing optically active aminoalcohols, in which the aminoalcohol is brought into contact with Raney cobalt in the presence of hydrogen. The patent teaches that high temperatures, e.g. above 160° C., decrease the racemate yield.

JP-A--06 135 906 (Derwent Abstract No. 94-197043/24; Chem. Abstracts 121: 179093z) describes a process for racemizing optically active vicinal primary diamines in the presence of hydrogen and a hydrogenation catalyst, for example Raney nickel and Raney cobalt.

DE-A-28 51 039 describes a process for preparing racemic mixtures of optically active 1-arylamines, in which the optically active 1-arylamines are treated with hydrogen in the presence of a hydrogenation catalyst, in particular Raney cobalt. DE-A-29 03 589 describes a process for preparing racemic mixtures of optically active amines, by treating the optically active amines with hydrogen in the presence of a hydrogenation catalyst, in particular Raney cobalt or Raney nickel, at elevated temperature. The reaction of optically active 2-amino-1-phenylpropane in the presence of a Raney cobalt catalyst with a reaction time of 12 hours leads, at a degree of racemization of a maximum of 98% to a racemate yield of only 91.1%.

The earlier German Application No. 19859775.4 of Dec. 23, 1998 relates to a process for racemizing optically active amines by reacting the optically active amine in the presence of hydrogen and a hydrogenation or dehydrogenation catalyst at elevated temperature by carrying out the reaction in the gas phase.

It is an object of the present invention to find an improved economical process for racemizing optically active amines in which the process product is obtained with high degree of racemization with simultaneously high racemization yield and high space-time yield.

We have found that this object is achieved by a process for racemizing optically active amines of the formula I

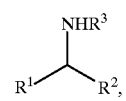
(I)

where $R^1$ and $R^2$ are different and $R^1$, $R^2$ and $R^3$ are alkyl, cycloalkyl, arylalkyl, aryl, heteroaryl or heterocyclic radicals and $R^3$, in addition, is hydrogen (H), where the radicals can bear substituents which are selected from the group consisting of alkyl, cycloalkyl, alkoxy, aryloxy, amino, alkylamino and dialkylamino, by reacting the optically active amine in the presence of hydrogen and a hydrogenation or dehydrogenation catalyst at elevated temperature which comprises carrying out the reaction in liquid phase and the catalyst comprising the catalytically active constituents copper, silver, iron, cobalt, nickel, ruthenium, rhodium, palladium, osmium, iridium and/or platinum and a support material which is selected from the group consisting of aluminum oxide, zirconium dioxide, titanium dioxide, carbon and/or oxygen compounds of silicon.

The process of the invention may be carried out in the liquid phase batchwise, or preferably continuously, as follows, in which case the catalyst is preferably disposed in the reaction as a fixed bed.

The process of the invention can be carried out in the absence, or preferably in the presence, of the amine of the formula $R^3NH_2$, where the radical $R^3$ corresponds to the radical $R^3$ of the optically active amine I (e.g. the amine ammonia in the event of racemization of optically active amines I where $R^3$=H.

If the process is carried out in the presence of the amine $R^3NH_2$, the molar ratio of $R^3NH_2$ to amine I is generally from 1:1 to 50:1, preferably from 1.5:1 to 30:1, particularly preferably from 2:1 to 20:1, very particularly preferably from 2:1 to 10:1. The $R^3NH_2$ excess based on the amine I can also be greater than 50:1.

The hydrogen is fed to the reaction generally in an amount of from 5 to 400 l, preferably in an amount of from 10 to 200 l, per mole of amine component I. The figures in liters each being converted to S.T.P.

The optically active amine I is passed in the liquid state over the catalyst in the presence of hydrogen and, advantageously, in the presence of the amine $R^3NH_2$, at pressures from 0.1 to 30 MPa, preferably from 5 to 25 MPa, particularly preferably from 10 to 25 MPa, which catalyst is usually in a preferably e xternally heated fixed-bed reactor, e.g. a tubular reactor.

When the procedure is carried out in a tubular reactor, it is possible for the flow to impinge the fixed catalyst bed either from above (e.g. trickle mode of operation) or from below (bottom mode of operation). A recirculated gas mode of operation is advantageous, in which case, for example, at a catalyst bed volume of 1 l, the gas recirculation rate of approximately from 0.01 to 1 m³/h (volume converted to S.T.P.) and an exhaust gas rate of approximately from 10 to 300 l/h being operated.

The catalyst space velocity is generally in the range from 0.05 to 2, preferably from 0.1 to 1, particularly preferably from 0.2 to 0.6, kg of amine I per liter of catalyst (bed volume) and hour.

The temperatures selected for the racemization are in the range from 100 to 300° C., preferably from 150 to 270° C., particularly preferably from 160 to 250° C., very particularly preferably from 170 to 240° C., in particular from 180 to 230° C.

The optically active amine I can be racemized in the presence of an inert solvent, which is also liquid under the reaction conditions selected, such as tetrahydrofuran, dioxane, N-methylpyrrolidone and/or ethylene glycol dimethyl ether.

It is possible to employ higher temperatures, higher overall pressures and higher catalyst space velocities than specified above. The pressure in the reaction vessel, which is essentially given by the sum of the partial pressures of the amine component I, the amine $R^3NH_2$ which may be present, the solvent which may be present and the racemized amine formed at the respective temperature employed, is expediently increased to the desired reaction pressure by injecting hydrogen.

From the reaction discharge, after this has expediently been expanded, the hydrogen, the amine of the formula $R^3NH_2$ which may have been used and the solvent which may have been used are removed (for example by distillation), in which case these can be recycled, and the resultant cooled crude reaction product, which essentially comprises the racemic amine I, is purified by fractional rectification, at atmospheric pressure or under reduced pressure.

Generally, in the process of the invention, the catalysts are used in the form of catalysts which consist only of catalytically active mass with or without a molding aid (for example graphite or stearic acid), if the catalyst is used as shaped body, that is comprise no other catalytically inactive accompanying materials.

In this contest, the materials used as catalyst supports
titanium dioxide ($TiO_2$; anatase, rutile),
aluminum oxide ($Al_2O_3$; preferably α-, β-, γ- or θ-$Al_2O_3$; D10-10 from BASF; $Al_2O_3$ having a large surface area prepared by contacting at least one precursor of aluminum oxide with at least one structure-forming compound in a liquid medium, e.g., according to German Application No. 197 30 126.6 of Jul. 14, 1997),
zirconium dioxide ($ZrO_2$; preferably in the monoclinic or tetragonal form),
silicon dioxide ($SiO_2$; for example produced by a precipitation from water glass or via the sol-gel process or mesoporic $SiO_2$, for example mesoporic $SiO_2$ having a mesopore specific surface area of at least 500 m²/g and a mesopore pore volume of at least 1.0 ml/g according to DE-A-196 39 016, or silica gel (for example according to Ullmann, Enzylk. Techn. Chem. [Encyclopedia of Industrial Chemistry], 4th Edition, Volume 21 (1982), pp. 457–63) or in the form of silicates, such as bentonite, montmorillonite, kaolin, hectorite or aluminosilicates (for example according to Nature, Volume 359 (1992), pp. 710–12, or alkali metal or alkaline earth metal aluminosilicates (zeolites), for example of the formula $M_{2/z}O \cdot Al_2O_3 \cdot xSiO_2 \cdot yH_2O$, where M is a monovalent or polyvalent metal, H, [$NH_4$], z is the valency, x=from 1.8 to approximately 12 and y=0 to approximately 8), magnesium silicates (for example stearite), zirconium silicates, cerium silicates or calcium silicates) or $SiO_2$ having a large surface area prepared by contacting at least one precursor of silicon dioxide with at least one structure-forming compound in a liquid medium, for example according to German Application No. 197 32 865.2 of Jul. 30, 1997),
and/or carbon (e.g. activated carbon or graphite in rod or tabletted form),
and their mixtures, are considered as belonging to the catalytically active mass.

The catalysts are used, for example, in such a manner that the catalytically active mass which is ground to powder is introduced into the reactor, or preferably that the catalytically active mass, after grinding, mixing with molding aids, molding and heating, is disposed in the reactor as shaped catalyst body—for example as tablets, beads, rings, extrudates (e.g. rods).

The concentration figures (in % by weight) of the components of the catalyst in each case relate—unless stated otherwise—to the catalytically active mass of the finished catalyst after its last heat treatment and prior to its reduction with hydrogen.

The catalytically active mass of the catalyst, after its last heat treatment and prior to its reduction with hydrogen, is defined as the sum of the masses of the catalytically active constituents and the abovementioned catalyst support materials and essentially comprises the constituents aluminum oxide ($Al_2O_3$) and/or zirconium dioxide ($ZrO_2$) and/or titanium dioxide ($TiO_2$) and/or carbon and/or oxygen compounds of silicon and one or more metals (oxidation state 0) or their organic or inorganic compounds which are reduced to the corresponding metal under the process conditions, for example oxides, selected from the group consisting of copper, silver, iron, cobalt, nickel, ruthenium, rhodium, palladium, osmium, iridium and/or platinum.

The sum of the abovementioned constituents of the catalytically active mass is customarily from 70 to 100% by weight, particularly from 80 to 100% by weight, in particular from 90 to 100% by weight, very particularly from 95 to 100% by weight, for example 100% by weight.

The catalytically active mass of the catalysts used in the process of the invention can, in addition, comprise one or more elements (oxidation state 0) or their inorganic or organic compounds selected from the groups consisting of I A to VI A and I B to VII B of Periodic Table of the Elements.

Examples of such elements and their compounds are:
Transition metals and their compounds, such as Re and rhenium oxides, Mn, $MnO_2$ and $Mn_2O_3$, Cr and chromium oxides, Mo and molybdenum oxides, W and tungsten oxides, Ta and tantalum oxides, Nb, niobium oxides and niobium oxalate, V, vanadium oxides and vanadyl pyrophosphate; lanthanides, such as Ce and $CeO_2$, Pr and $Pr_2O_3$; alkali metal oxides, such as $Na_2O$; alkali metal carbonates; alkaline earth metal oxides, such as MgO, CaO, SrO, BaO; alkaline earth metal carbonates, such as $MgCO_3$, $CaCO_3$ and $BaCO_3$; boron oxide ($B_2O_3$).

The catalytically active mass of the catalysts used in the process of the invention comprises the catalytically active constituents copper, silver, iron, cobalt, nickel, ruthenium, rhodium, palladium, osmium, iridium and/or platinum in total in amounts of generally from 0.1 to 80% by weight, preferably from 0.1 to 70% by weight, particularly preferably from 0.1 to 60% by weight, calculated as metal in oxidation state 0.

In addition, the catalytically active mass comprises the support materials aluminum oxide ($Al_2O_3$), zirconium dioxide ($ZrO_2$), titanium dioxide ($TiO_2$), carbon and/or oxygen compounds of silicon, calculated as $SiO_2$, in total in amounts generally from 20 to 99.9% by weight, preferably from 30 to 99.9% by weight.

Examples of such catalysts are the catalysts disclosed in EP-A-839 575 which comprise, based on the total weight of the catalyst, more than 6 and up to 50% by weight of cobalt, nickel or their mixture, from 0.001 to 25% by weight of ruthenium, from 0 to 10% by weight of copper and from 0 to 5% by weight of promoters on a porous metal oxide support, for example aluminum oxide, aluminosilicate, titanium dioxide, zirconium dioxide or mixtures thereof, which can be prepared by (a) impregnating the support with the metals, promoters or compounds thereof, (b) drying and calcining the impregnated support and (c) reducing the calcined support in a hydrogen stream, the catalysts disclosed in EP-A-839 574 comprising, based on the total weight of the catalyst, from 0.1 to 6% by weight of cobalt, nickel or their mixture, from 0.001 to 25% by weight of ruthenium, from 0 to 10% by weight of copper and from 0 to 5% by weight of promoters on a porous metal oxide support, for example aluminum oxide, aluminosilicate, titanium dioxide, zirconium dioxide or mixtures thereof, which can be prepared by (a) impregnating the support with the metals, promoters or compounds thereof, (b) drying and calcining the impregnated support and (c) reducing the calcined support in a hydrogen stream, and what are termed shell catalysts, in which the catalytically active mass is applied in the form of a shell to a core of support material which is generally inert under the reaction conditions, such as quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or mixtures thereof.

To prepare such shell catalysts, customarily, impregnation processes are used, as are described in J.-P. Le Page et al., Applied Heterogeneous Catalysis, Edition Technip Paris, (1987), ISBN 2-7108-0531-6, pages 106–123. These impregnation processes comprise (a) an impregnation of the support material with an excess of solution (immersion) or (b) a spray-impregnation of the support material in an impregnating drum and in each case the subsequent drying and calcining.

Another possibility for preparing such shell catalysts is described, for example, in DE-A-16 42 938 and DE-A-17 69 998. According to this, an aqueous-solvent- and/or an organic-solvent-containing solution or suspension of the constituents of the catalytically active mass and/or its precursor compounds, which is termed 'slurry' below, is sprayed onto the support material at elevated temperature in a heated coating drum until the described content of catalytically active mass in the total catalyst weight is achieved. According to DE-A-21 06 796, the coating can also be carried out in fluidized coaters, as are described, for example, in DE-A-12 80 756. The slurry may comprise, in accordance with the teaching of EP-A-744 214, organic binders, preferably copolymers, for example vinyl acetate/vinyl laurate and vinyl acetate/ethylene.

Examples of shell catalysts usable in the process of the invention are the catalysts which are disclosed in DE-A-20 59 978, Example 1 (catalyst A) and are prepared by impregnating alumina agglomerates with an aqueous noble metal salt solution, for example Pd salt solution, and subsequent drying and calcination, and the catalysts which are disclosed in the abovementioned article by J.-F. Le Page et al (Applied Heterogeneous Catalysis) for example on page 110, and are prepared by impregnation and comprise $Al_2O_3$ and Ni and/or Co.

In the process of the invention, preferably, catalysts are used whose catalytically active mass after the last heat treatment and prior to the reduction with hydrogen comprises from 20 to 85% by weight, preferably from 25 to 80% by weight, particularly preferably from 30 to 75% by weight, of aluminum oxide ($Al_2O_3$) and/or zirconium dioxide ($ZrO_2$) and/or titanium dioxide ($TiO_2$) and/or carbon (e.g. as activated carbon or graphite) and/or oxygen compounds of silicon, calculated as $SiO_2$, from 1 to 70% by weight, preferably from 2 to 65% by weight, particularly preferably from 4 to 60% by weight, very particularly preferably from 20 to 60% by weight, of oxygen compounds of copper, calculated as CuO, from 0 to 70% by weight, preferably from 1 to 70% by weight, particularly preferably from 5 to 60% by weight, of oxygen compounds of nickel, calculated as NiO, and from 0 to 50% by weight, preferably from 0 to 30% by weight, for example from 0.1 to 25% by weight, of oxygen compounds of cobalt, calculated as CoO, oxygen compounds of chromium, calculated as $Cr_2O_3$, oxygen compounds of zinc, calculated as ZnO, oxygen compounds of molybdenum, calculated as $MoO_3$, oxygen compounds of manganese, calculated as $MnO_2$, oxygen compounds of magnesium, calculated as MgO, oxygen compounds of calcium, calculated as CaO, and/or oxygen compounds of barium, calculated as BaO.

Examples of such catalysts are the catalysts which are disclosed in DE-A-19 53 263 and comprise cobalt, nickel and copper and aluminum oxide and/or silicon dioxide having a metal content of from 5 to 80% by weight, based on the total catalyst, where the catalysts, calculated on the metal content, comprise from 70 to 95% by weight of a mixture of cobalt and nickel and from 5 to 30% by weight of copper and where the weight ratio of copper to nickel is from 4:1 to 1:4, for example the catalysts which are described in the examples in loc. cit. and comprise from 2 to 4% by weight of copper oxide, 10% by weight of cobalt oxide and 10% by weight of nickel oxide on aluminum oxide, the catalysts disclosed in EP-A-382 049 whose catalytically active mass prior to the reduction with hydrogen comprises from 20 to 85% by weight of $ZrO_2$, from 1 to 30% by weight CuO and in each case from 1 to 40% by weight of CoO and NiO, for example the catalysts which are described in loc. cit. on page 6 and have the composition 76% by weight of Zr, calculated as $ZrO_2$, 4% by weight of Cu, calculated as CuO, 10% by weight of Co, calculated as CoO, and 10% by weight of Ni, calculated as NiO, the catalysts disclosed in EP-A-696 572 whose catalytically active mass prior to the reduction with hydrogen comprises from 20 to 85% by weight of $ZrO_2$, from 1 to 30% by weight of oxygen compounds of copper, calculated as CuO, from 30 to 70% by weight of oxygen compounds of nickel, calculated as NiO, from 0.1 to 5% by weight of oxygen compounds of molybdenum, calculated as $MoO_3$, and from 0 to 10% by weight of oxygen compounds of aluminum and/or of manganese, calculated as $Al_2O_3$ or $MnO_2$, for example the catalyst which is disclosed in loc. cit. page 8, and has the composition 31.5% by weight of $ZrO_2$, 50% by weight of NiO, 17% by weight of CuO and 1.5% by weight of $MoO_3$, the catalysts which are disclosed in German Application No. 19826396.1 of Jun. 12, 1998 and whose catalytically active mass prior to the reduction of hydrogen comprises from 22 to 40% by weight of $ZrO_2$, from 1 to 30% by weight of oxygen compounds of copper, calculated as CuO, from 15 to 50% by weight of oxygen compounds of nickel, calculated as NiO, where the molar Ni:Cu ratio is greater than 1, from 15 to 50% by weight of oxygen compounds of cobalt, calculated as CoO, from 0 to 10% by weight of oxygen compounds of aluminum and/or of manganese, calculated as $Al_2O_3$ or $MnO_2$, and no oxygen compounds of molybdenum, for example the catalyst (A) which is disclosed in loc. cit., page 17, and has the composition 33% by weight of Zr, calculated as $ZrO_2$, 28% by weight of Ni, calculated as NiO, 11% by weight of Cu, calculated as CuO and 28% by weight of Co, calculated as CoO, the catalysts which are disclosed in German Application No. 19742911.4 of Sep. 29, 1997 and whose catalytically active mass prior to the reduction with hydrogen comprises from 20 to 85% by weight of $ZrO_2$, from 1 to 30% by weight of oxygen compounds of copper, calculated as CuO, from 14 to 70% by weight of oxygen compounds of nickel, calculated as NiO, where the Ni:Cu ratio is greater than 1, from 0 to 10% by weight of oxygen compounds of aluminum and/or of manganese, calculated as $Al_2O_3$ or $MnO_2$, and no oxygen compounds of cobalt or molybdenum, for example the catalyst (A) which is disclosed in loc. cit., pages 14 to 15, and has the composition 32% by weight of Zr, calculated as $ZrO_2$, 51% by weight of Ni, calculated as NiO, and 17% by weight of Cu, calculated as CuO, the catalysts of the formula $M_xMg_y(SiO_2) \cdot nH_2O$ which are disclosed in EP-A-284 919, where M is a divalent, reducible metal atom selected from the group consisting of Cu, Fe, Co and Ni, x and y are numbers which together can reach 1.5, and n, after drying, is between 0 and 80 expressed in % by weight, for example the catalyst which is described in loc. cit. in the example and comprises 35% of CuO, 9% of MgO and 38% of $SiO_2$ and the catalyst which is described in EP-A-863 140 on page 3 and comprises from 45 to 47% by weight of CuO, magnesium silicate of about from 15 to 17% by weight of MgO and 35 to 36% by weight of $SiO_2$, about 0.9% by weight of $Cr_2O_3$, about 1% by weight of BaO and about 0.6% by weight of ZnO, the catalysts which are disclosed in DE-A-24 45 303 and are obtainable by heating a basic copper- and aluminum-containing carbonate of the general composition $Cu_mAl_6(CO_3)_{0.5m}O_3(OH)_{m+12}$, where m is any, even non-integral value from 2 to 6, at from 350 to 700° C., for example the copper-containing precipitated catalyst which is disclosed in loc. cit., Example 1, and is prepared by treating a solution of copper nitrate and aluminum nitrate with sodium bicarbonate and subsequent washing, drying and heating the precipitate, the supported catalysts which are disclosed in WO 95/32171 and EP-A-816 350 and comprise from 5 to 50, preferably from 15 to 40, % by weight of copper, calculated as CuO, from 50 to 95, preferably from 60 to 85% by weight of silicon, calculated as $SiO_2$, from 0 to 20% by weight of magnesium, calculated as MgO, from 0 to 5% by weight of barium, calculated as BaO, from 0 to 5% by weight of zinc, calculated as ZnO, and from 0 to 5% by weight of chromium, calculated as $Cr_2O_3$, in each case based on the total weight of the calcined catalyst, for example the catalyst which is disclosed in EP-A-816 350, page 5, and comprises 30% by weight of CuO and 70% by weight of $SiO_2$, the catalysts which are disclosed in EP-A-514 692 and whose catalytically active mass prior to the reduction with hydrogen comprises from 5 to 100% by weight of an oxide of copper and nickel in an atomic ratio of from 1:1 to 10:1 and zirconium and/or aluminum oxide, in particular the catalysts which are disclosed in loc. cit. on page 3, lines 20 to 30, and whose catalytically active mass prior to the reduction with hydrogen comprises from 20 to 80, particularly from 40 to 70, % by weight of $Al_2O_3$ and/or $ZrO_2$, from 1 to 30% by weight of CuO, from 1 to 30% by weight of NiO with or without from 1 to 30% by weight of CoO, for example the catalyst which is described in loc. cit., Example 1, and consists (after the activation) of 55% by weight of $Al_2O_3$, 36% by weight of Cu and 7% by weight of Ni, the catalysts which are disclosed in EP-A-691 157 and consist (prior to the reduction with $H_2$) of from 85 to 100, in particular from 95 to 100, % by weight of copper oxide and zirconium dioxide and from 0 to 15, in particular from 0 to 5, % by weight of metal oxides of subgroups Ib to VIIb and VIII of the Periodic Table of the Elements, for example the catalyst which is described in loc. cit., pages 5 to 6, and has the composition 52.6% by weight of CuO and 47.4% by weight of $ZrO_2$, and the catalysts which are disclosed in German Application No. 19859776.2 of Dec. 23, 1998 and comprise copper and oxygen compounds of titanium, where the catalyst is used in the form of shaped bodies which were produced with addition of metallic copper powder. For example, catalysts whose catalytically active mass prior to the reduction with hydrogen comprises from 20 to 83% by weight of oxygen compounds of titanium, calculated as $TiO_2$, from 15 to 60% by weight of oxygen compounds of copper, calculated as CuO, and from 2 to 29% by weight of metallic copper which was added prior to the molding of the catalyst material.

Preferably, in the process of the invention, catalysts are used whose catalytically active mass comprises less than 20% by weight, preferably less than 10% by weight, in particular less than 5% by weight, very particularly less than 1% by weight, of cobalt, calculated as CoO. Very particularly preferably, the catalytically active mass comprises no catalytically active amounts of cobalt or its compounds.

Particularly preferably, in the process of the invention, catalysts are used whose catalytically active mass after the last heat treatment and prior to the reduction with hydrogen comprises from 20 to 85% by weight, preferably from 25 to 80% by weight, particularly preferably from 30 to 75% by weight, of aluminum oxide ($Al_2O_3$) and/or zirconium dioxide ($ZrO_2$) and/or titanium dioxide ($TiO_2$) and/or oxygen compounds of silicon, calculated as $SiO_2$.

In particular, catalysts are used whose catalytically active mass after the last heat treatment and prior to the reduction with hydrogen comprises from 35 to 75% by weight of aluminum oxide ($Al_2O_3$), from 20 to 60% by weight of oxygen compounds of copper, calculated as CuO, and from 5 to 45% by weight, preferably from 5 to 20% by weight, of oxygen compounds of nickel, calculated as NiO, where the sum of these components is at least 80% by weight, preferably at least 90% by weight, particularly preferably at least 95% by weight, for example 100% by weight.

Such catalysts can be prepared, for example, according to EP-A-514 692, page 3, lines 24 to 30. For example, loc. cit., Example 1, describes a catalyst consisting (after the activation) of 55% by weight of $Al_2O_3$, 36% by weight of Cu and 7% by weight of Ni.

To prepare the catalysts used in the process of the invention, various processes are possible.

They are obtained, for example, by peptizing pulverulent mixtures of the hydroxides, carbonates, oxides and/or other salts of the catalyst components with water and subsequent extrusion and tempering of the resultant mass.

The catalysts used in the process of the invention can also be produced by impregnating the catalyst support materials or mixtures of two or more of these catalyst support materials which are present, for example, in the form of powder or shaped bodies, such as rods, tablets, beads or rings.

Shaped bodies of the abovementioned catalyst support materials can be produced by the customary processes.

The catalyst support material is likewise impregnated by the customary processes, as described, for example, in EP-A-599 180, EP-A-673 918 or A. B. Stiles, Catalyst Manufacture—Laboratory and Commercial Preparations, Marcel Dekker, New York (1983), by applying an in each case corresponding metal salt solution in one or more impregnation stages, where the metal salts used are for example, corresponding nitrates, acetates or chlorides. The mass, subsequently to the impregnation, is dried and if appropriate calcined.

The impregnation can be performed by what is termed the incipient wetness method, in which the catalyst support material is moistened, in accordance with its water absorption capacity, at most up to saturation with the impregnation solution. However, the impregnation can also be performed in supernatant solution.

In the case of multistage impregnation processes, it is expedient to dry and, if appropriate, to calcine the support material between individual impregnation steps. The multistage impregnation is advantageously to be employed particularly if the catalyst support material is to be charged with a relatively large amount of metal.

To apply a plurality of metal components to the catalyst support material, the impregnation can be carried out simultaneously with all metal salts or successively in any sequence of the individual metal salts.

In addition, precipitation methods can also be employed to prepare catalysts used in the process of the invention. Thus, they can, for example, be produced by a joint precipitation of the metal components from an aqueous salt solution comprising these elements by means of mineral bases in the presence of a slurry or suspension of fine-grained powders of the sparingly soluble catalyst support material and subsequent washing, drying and calcining of the resultant precipitate. The sparingly soluble catalyst support material used can be, for example, aluminum oxide, titanium dioxide, silicon dioxide, zirconium dioxide and/or zirconium oxide hydrate.

The catalysts used in the process of the invention can be prepared by a joint precipitation (coprecipitation) of all of their components. For this purpose, expediently, an aqueous mineral base, in particular an alkali metal base—for example sodium carbonate, sodium hydroxide, potassium carbonate or potassium hydroxide–is added to the aqueous salt solution comprising the catalyst components with heating and stirring until the precipitation is complete. The type of salts used is generally not critical: since in this procedure it is principally the water solubility of the salts which is relevant, one criterion is their high water solubility, which is required to prepare these relatively highly concentrated salt solutions. Obviously, in the selection of the salts of the individual components, clearly the only salts which are selected are those having anions which do not lead to interferences, either by causing unwanted precipitations or by hindering or preventing the precipitation by complex formation.

The precipitates obtained in these precipitation reactions are generally non-uniform chemically and consist, inter alia, of mixtures of the oxides, oxide hydrates, hydroxides, carbonates, and insoluble and basic salts of the metals used. It can prove to be favorable for the filterability of the precipitates if they are aged, i.e. if they are allowed to stand for some time after the precipitation, possibly heated or with air being passed through them.

The precipitates obtained by these precipitation methods are further processed as usual to give the catalysts. After washing, they are generally dried at from 80 to 200° C., preferably at from 100 to 150° C., and then calcined. The calcination is generally carried out at from 300 to 800° C., preferably from 400 to 600° C., in particular from 450 to 550° C.

After the calcination, the catalyst is expediently conditioned either by grinding it to a defined particle size or, after it has been ground, mixing it with molding aids such as graphite or stearic acid, pressing it by means of a press to give moldings, e.g. tablets, and heating it. The heating temperatures generally correspond here to the temperatures during calcination.

The catalysts prepared in this manner comprise the catalytically active metals in the form of a mixture of their oxygen compounds, i.e. in particular as oxides and mixed oxides.

The catalysts prepared in this manner are customarily prereduced before their use for racemizing the optically active amines I. However, they can also be used without a prereduction, in which case they are then reduced under the racemization conditions by the hydrogen present in the reactor.

For the prereduction, the catalysts are generally first exposed to a nitrogen/hydrogen atmosphere at from 150 to 200° C. for a period of from 12 to 20 hours and then further treated in a hydrogen atmosphere for up to approximately 24 hours at from 200 to 400° C. In this prereduction, some of the oxygen compounds of the metals present in the catalysts are reduced to give the corresponding metals, so that these together with the different types of oxygen compounds are present in the active form of the catalyst.

The radicals $R^1$, $R^2$ and $R^3$ of the optically active amines of the formula I used in the process of the invention

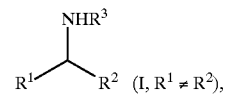

where $R^1$ and $R^2$ are different, independently of one another are alkyl, cycloalkyl, arylalkyl, aryl, heteroaryl, and heterocyclic radicals and $R^3$ is in addition hydrogen, where the radicals can be substituted by substituents which are inert under the reaction conditions and are selected from the group consisting of alkyl, cycloalkyl, alkoxy, aryloxy, amino, alkylamino and dialkylamino.

$R^1$, $R^2$ and $R^3$ are preferably:
  unbranched or branched alkyl, such as $C_{1-20}$-alkyl, particularly preferably $C_{1-12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, 2-ethylhexyl, n-nonyl, isononyl, n-decyl, isodecyl, n-undecyl, n-dodecyl, isododecyl, very particularly preferably $C_{1-8}$-alkyl, such as methyl, ethyl, n-propyl, isopropyl, n-butyl, isobutyl, sec-butyl, tert-butyl and 2-ethylhexyl,
  cycloalkyl radical, preferably $C_{3-8}$-cycloalkyl, such as cyclopropyl, cyclobutyl, cyclopentyl, cyclohexyl, cycloheptyl and cyclooctyl, particularly preferably cyclopentyl, cyclohexyl and cyclooctyl, very particularly preferably cyclopentyl and cyclohexyl,
  arylalkyl radical, preferably $C_{7-20}$-arylalkyl, such as benzyl, 1-phenethyl, 2-phenethyl, 1-naphthylmethyl, 2-naphthylmethyl, phenanthrylmethyls, 4-tert-butylphenylmethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, aromatic radical, preferably $C_{6-20}$-aryl, such as phenyl, 1-naphthyl, 2-naphthyl, 1-anthryl, 2-anthryl, 9-anthryl, particularly preferably phenyl, 1-naphthyl and 2-naphthyl, particularly preferably phenyl, heteroaromatic radical, preferably $C_{3-15}$-heteroaryl, such as 2-pyridinyl, 3-pyridinyl, 4-pyridinyl, quinolinyl, pyrazinyl, pyrrol-3-yl, thientyl, imidazol-2-yl, 2-furanyl and 3-furanyl, and heterocyclic radical, preferably $C_{3-15}$-heterocycloalkyl, such as N-alkylpiperidin-3-yl, N-alkylpiperidin-4-yl, N,N'-dialkylpiperazin-2-yl, tetrahydrofuran-3-yl and N-alkylpyrrolidin-3-yl, where in these cases the radicals R independently of one another may bear substituents which are inert under the reaction conditions, for example $C_{1-20}$-alkyl, $C_{3-8}$-cycloalkyl, $C_{1-20}$-alkoxy, $C_{6-20}$-aryloxy, amino, $C_{1-20}$-alkylamino and $C_{2-20}$-dialkylamino.

The number of these substituents here in R, depending on the type of the radical, can be from 0 to 5, preferably from 0 to 3, in particular 0, 1 or 2. Suitable substituents are, in particular:

$C_{1-20}$-alkyl, as defined above, $C_{3-8}$-cycloalkyl, as defined above, $C_{1-20}$-alkoxy, preferably $C_{1-8}$-alkoxy, such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy, particularly preferably $C_{1-4}$-alkoxy, such as methoxy, ethoxy, n-propoxy, isopropoxy, n-butoxy, isobutoxy, sec-butoxy and tert-butoxy, $C_{6-20}$-aryloxy, such as phenoxy, 1-naphthoxy and 2-naphthoxy, preferably phenoxy, amino (—$NH_2$), $C_{1-20}$-alkylamino, preferably $C_{1-12}$-alkylamino, particularly $C_{1-8}$-alkylamino, such as methylamino, ethylamino, n-propylamino, isopropylamino, n-butylamino, isobutylamino, tert-butylamino, cyclopentylamino, cyclohexylamino, and $C_{2-20}$-dialkylamino, preferably $C_{2-12}$-dialkylamino, particularly $C_{2-8}$-dialkylamino, such as N,N-dimethylamino, N,N-diethylamino, N,N-di-n-propylamino, N,N-di-isopropylamino, N,N-di-n-butylamino, N-ethyl-N-methylamino, N-methyl-N-propylamino, dicyclohexylamino.

$R^3$, very particularly preferably, is hydrogen (H).

Examples of amines I which can be used in the process of the invention are:

1-methoxy-2-aminopropane (MOIPA), 2-amino-3-methylbutane, 2-amino-3,3-dimethylbuatne, 1-phenylethylamine, 1-naphthylethylamine, 2-naphthylethylamine, 1-phenylpropylamine, 2-amino-1-phenylpropane, 2-amino-1-(p-hydroxyphenyl) propane, 2-amino-1-(p-trifluoromethylphenyl)propane, 2-amino-1-cyclohexylpropane, 2-amino-6-methylheptane, 2-aminoheptane, 2-amino-4-methylhexane, 1-(4-methylphenyl)ethylamine, 1(4-methoxyphenyl)ethylamine, 1-(3-methoxyphenyl) ethylamine, 1-aminotetralin, trans-1-amino-2-benzyloxycyclopentane and trans-1-amino-2-benzyloxycyclohexane.

Particular preference is given to 1-methoxy-2-aminopropane, 2-amino-3-methylbutane and 2-amino-3,3-dimethylbutane.

In a particular variant, in the process of the invention an optically active amine I is used which was obtained by cleaving an amide derived from this optically active amine, which amide arises in the preparation of the corresponding enantiomer of I (based on the asymmetric carbon shown in I) by (a) enantioselective acylation of the racemic amine I with an ester, the acid component of which ester bears a fluorine, nitrogen, phosphorus, oxygen or sulfur adjacent to the carbonyl carbon, in the presence of a hydrolase and (b) separation of the resultant mixture of optically active amine I and amide.

In a further particular variant, an optically active amine I is used in the process of the invention, which amine was obtained in the preparation of the corresponding enantiomer of I (based on the asymmetric carbon shown in I) by (a) enantioselective acylation of the racemic amine I with an ester, the acid component of which bears a fluorine, nitrogen, phosphorus, oxygen or sulfur adjacent to the carbonyl carbon, in the presence of a hydrolase, (b) separation of the resultant mixture of optically active amine I and amide and (c) isolation of the corresponding other enantiomer of I by cleavage of the amide.

The processes for preparing optically active amines I from the corresponding racemates by (a) enantioselective acylation of the racemic amine I with an ester, the acid component of which bears a fluorine, nitrogen, phosphorus, oxygen or sulfur adjacent to the carbonyl carbon, in the presence of a hydrolase and (b) separation of the resultant mixture of optically active amine I and amide and (c) isolation of the corresponding other enantiomer I by cleavage of the amide are described in WO 95/08636 and WO 96/23894.

The hydrolase is, for example, a lipase, in particular a microbial lipase. The ester is, for example, a $C_{1-12}$-alkylester of $C_{1-4}$-alkoxyacetic acids, such as ethyl methoxyacetate.

The amide which is derived from the optically active amine I can be cleaved with retention of the configuration of the chirality center of hydrolysis, for example by hydrolysis in the presence of a polyol or an aminoalcohol and an alkali metal hydroxide or alkaline earth metal hydroxide according to WO 97/10201.

These particular process variants prove to be particularly economical, since, after the preparation of the wanted enantiomer of the amine I, for example according to WO 95/08636 or WO 96/23894, the remaining unwanted enantiomer of I is racemized according to the processes of this application and used again in the processes for preparing the wanted enantiomer of I, for example according to WO 95/08636 or WO 96/23894. In this manner, it is possible to obtain in total more than 50% of the wanted enantiomer from the racemic amine I. (In this context, compare also the details on page 1 of the description, 2nd paragraph).

EXAMPLES

Example 1

Racemizing S-pinacolylamine (2,2-dimethyl-3-aminobutane) batchwise in the liquid phase 25 g of S-pinacolylamine (99% ee) were stirred for 6 h at 200° C. and 150 bar together with 31 ml of ammonia and 5 g of catalyst having the composition 10% of NiO, 10% of CoO, 4% of CuO and 76% of $Al_2O_3$ in the presence of hydrogen.

The reaction effluent was analyzed by gas chromatography. The enantiomer ratio was determined via a chiral HPLC column.

Enantiomeric excess: 2.4%

GC analysis of the effluent (ammonia-free and anhydrous) in % GC peak area:

| pinacolone | 0.1 |
|---|---|
| pinacolylamine | 99.2 |
| pinacolol | 0.5 |
| others | 0.2 |
| degree of racemization: | 97.6% |
| racemate yield: | 99.2% | degree of racemization: 97.6% racemate yield: 99.2%

Example 2

Racemizing S-pinacolylamine (2,2-dimethyl-3-aminobutane) batchwise in the liquid phase 25 g of (S)-pinacolylamine (99% ee) were stirred for 6 h at 200° C. and 150 bar in the presence of hydrogen together with 31 ml of ammonia and 5 g of catalyst having the composition 50% by weight of NiO, 30% by weight of $ZrO_2$, 18% by weight of CuO, 1.5% by weight of $MoO_3$ and 0.2% by weight of $Na_2O$.

The reaction effluent was analyzed as in Example 1.

Enantiomeric excess: 1.1%

GC analysis of the effluent (ammonia-free and anhydrous) in % of GC peak area:

| pinacolone | <0.1 |
|---|---|
| pinacolylamine | >98.5 |
| pinacolol | 0.5 |
| others | 1 |
| degree of racemization: | 98.9% |
| racemate yield: | 98% | degree of racemization: 98.9% racemate yield: 98%

Comparative Example 1

Experiment on racemizing (R)-MOIPA in the liquid phase in a similar manner to DE-A-29 03 589

10 g of (R)-MOIPA (112 mmol), 70 ml of tetrahydrofuran and 1 g of Raney cobalt were charged into a 0.3 l autoclave. A pressure of 20 bar was set using hydrogen. The autoclave was heated to 160° C. and the $H_2$ pressure increased to 50 bar. After 12 h under these conditions, the mixture was cooled to room temperature, the catalyst filtered off and the tetrahydrofuran taken off on a rotary evaporator. The amount of residue was 2.5 g.

Determination of the enantiomer excess (ee) by HPLC analysis: 4.8%

(S)-MOIPA=47.6% of peak area (R)-MOIPA=52.4% of peak area

GC analysis [% of peak area]:

tetrahydrofuran: 0.2 methoxyisopropanol: 2.2

(R)-+(S)-MOIPA: 68.3 octylamine: 3.7 octanol: 10.0 sum of unknown compounds: 15.6 degree of racemization: 90% racemate yield: 61%

Comparative Example 2

Experiment on racemizing (S)-3,3-dimethyl-2-aminobutane (pinacolylamine) in the liquid phase in a similar manner to DE-A-29 03 589

10 g of (S)-pinacolylamine (99% ee) were mixed together with 60 g of THF and 1 g of Raney cobalt in a 0.3 l tubular autoclave and stirred under a hydrogen atmosphere at a pressure of 50 bar and a temperature of 165° C. for 12 h.

The reactor contents were then cooled to room temperature, separated off from the catalyst and the enantiomeric ratio was determined via a chiral HPLC column.

Enantiomeric excess: 84%

GC analysis of the effluent (ammonia-free and anhydrous) in % of GC peak area:

| pinacolone | <0.1 |
|---|---|
| pinacolylamine | 92.7 |
| pinacolol | 4.3 |
| others | 2.9 |
| degree of racemization: | 3% | degree of racemization: 3% racemate yield: 92.7%

We claim:

1. A process for racemizing optically active amines of the formula I

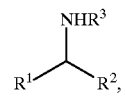

(I)

where $R^1$ and $R^2$ are different and $R^1$, $R^2$ and $R^3$ are alkyl, cycloalkyl, arylalkyl, aryl, heteroaryl or heterocyclic radicals and $R^3$, in addition, is hydrogen, where the radicals can bear substituents which are selected from the group consisting of alkyl, cycloalkyl, alkoxy, aryloxy, amino, alkylamino and dialkylamino, by reacting the optically active amine in the presence of hydrogen and a hydrogenation or dehydrogenation catalyst at elevated temperature which comprises carrying out the reaction in liquid phase and in the presence of a catalyst whose catalytically active mass prior to reduction with hydrogen comprises from 20 to 85% by weight of aluminum oxide ($Al_2O_3$), zirconium dioxide ($ZrO_2$), titanium dioxide ($TiO_2$), carbon and/or oxygen compounds of silicon, calculated as $SiO_2$, from 1 to 70% by weight of oxygen compounds of copper, calculated as CuO, from 0 to 70% by weight of oxygen compounds of nickel, calculated as NiO, and from 0 to 50% by weight of oxygen compounds of cobalt, calculated as CoO, oxygen compounds of chromium, calculated as $Cr_2O_3$, oxygen compounds of zinc, calculated as ZnO, oxygen compounds of molybdenum, calculated as $MoO_3$, oxygen compounds of manganese, calculated as $MnO_2$, oxygen compounds of magnesium, calculated as MgO, oxygen compounds of calcium, calculated as CaO and/or oxygen compounds of barium, calculated as BaO.

2. A process as claimed in claim 1, wherein the reaction is carried out in the presence of an amine of the formula $R^3NH_2$, where the radical $R^3$ corresponds to the radical $R^3$ of the optically active amine I.

3. A process as claimed in either of claims 1 and 2, wherein the reaction is carried out in the presence of a catalyst whose catalytically active mass prior to reduction with hydrogen comprises from 35 to 75% by weight of aluminum oxide ($Al_2O_3$), from 20 to 60% by weight of oxygen compounds of copper, calculated as CuO, and from 5 to 45% by weight of oxygen compounds of nickel, calculated as NiO, where the sum of these compounds is at least 80% by weight of the entire catalyst.

4. A process as claimed in either of claims 1 and 2, wherein the reaction is carried out in the presence of a catalyst whose catalytically active mass comprises less than 20% by weight of cobalt, calculated as CoO.

5. A process as claimed in either of claims 1 and 2, wherein the reaction is carried out at temperatures of from 150 to 170° C.

6. A process as claimed in either of claims 1 and 2, wherein the reaction is carried out at pressures of from 0.1 to 30 MPa.

7. A process as claimed in either of claims 1 and 2, wherein the optically active amine is 1-methoxy-2-aminopropane, 2-amino-3-methylbutane or 2-amino-3,3-dimethylbutane.

8. A process as claimed in either of claims 1 and 2, wherein the optically active amine I was obtained by cleavage of an amide derived from this optically active amine, which amide arises in the preparation of the corresponding enantiomer of I by (a) enantioselective acylation of the racemic amine I with an ester, the acid component of which ester bears a fluorine, nitrogen, phorphorus, oxygen or sulfur adjacent to the carbonyl carbon, in the presence of a hydrolase and (b) separation of the resultant mixture of optically active amine I and amide.

9. A process according to either of claims 1 and 2, wherein the optically active amine I was obtained in the preparation of the corresponding enantiomer of I by (a) enantioselective acylation of the racemic amine I with an ester, the acid component of which ester bears a fluorine, nitrogen, phosphorus, oxygen or sulfur adjacent to the carbonyl carbon, in the presence of a hydrolase, (b) separation of the resultant mixture of optically active amine I and amide and (c) isolation of the corresponding other enantiomer of I by cleavage of the amide.

\* \* \* \* \*

UNITED STATES PATENT AND TRADEMARK OFFICE
CERTIFICATE OF CORRECTION

PATENT NO. : 6,153,797
DATED : November 28, 2000
INVENTOR(S) : Reichers et al.

It is certified that error appears in the above-identified patent and that said Letters Patent is hereby corrected as shown below:

Title page,
Item [30], the priority number should be -- 199 05 838 --.

Column 15, claim 5,
Line 19, "170" should be -- 270 --.

Column 16, claim 8,
Line 9, "phorphorus" should be -- phosphorus --.

Signed and Sealed this

Twenty-fifth Day of September, 2001

Attest:

NICHOLAS P. GODICI
Attesting Officer     Acting Director of the United States Patent and Trademark Office